United States Patent
Hong (10) Patent No.: US 11,893,809 B2
(45) Date of Patent: Feb. 6, 2024

(54) RE-IDENTIFICATION OF ROUGH GEMSTONES

(71) Applicant: De Beers UK Ltd, London (GB)

(72) Inventor: Qi He Hong, Surrey (GB)

(73) Assignee: De Beers UK Ltd, London (GB)

(*) Notice: Subject to any disclaimer, the term of this patent is extended or adjusted under 35 U.S.C. 154(b) by 39 days.

(21) Appl. No.: 17/620,477

(22) PCT Filed: May 21, 2020

(86) PCT No.: PCT/EP2020/064226
§ 371 (c)(1),
(2) Date: Dec. 17, 2021

(87) PCT Pub. No.: WO2020/254058
PCT Pub. Date: Dec. 24, 2020

(65) Prior Publication Data
US 2022/0254174 A1 Aug. 11, 2022

(30) Foreign Application Priority Data
Jun. 20, 2019 (GB) ...................................... 1908875

(51) Int. Cl.
*G06V 20/64* (2022.01)
*G06V 10/46* (2022.01)
(Continued)

(52) U.S. Cl.
CPC ............ *G06V 20/647* (2022.01); *G06V 10/46* (2022.01); *G06V 10/54* (2022.01); *G06V 10/758* (2022.01)

(58) Field of Classification Search
CPC ...... A44C 17/00; G01N 21/87; G01N 33/381; G01N 21/88; G01N 2021/8477;
(Continued)

(56) References Cited

U.S. PATENT DOCUMENTS

2004/0112087 A1 6/2004 Bishop
2005/0187831 A1* 8/2005 Gershburg ........... G06Q 10/087
705/27.2
(Continued)

FOREIGN PATENT DOCUMENTS

WO  02/11031 A1   2/2002
WO  03/099054 A2  12/2003
(Continued)

OTHER PUBLICATIONS

Keith Forbes, "Calibration, Recognition, and Shape from Silhouettes of Stones", Jun. 2007, The University of Cape Town, PhD Thesis, Department of Electrical Engineering, 257 pages. (Year: 2007).*

(Continued)

*Primary Examiner* — Michael J Vanchy, Jr.

(57) ABSTRACT

A method of re-identifying a rough gemstone comprises providing a 3D model of a first rough gemstone; generating a series of virtual 2D silhouette images of the 3D model; processing each 2D image of the series of virtual 2D silhouette images to obtain a dataset associated with the first rough gemstone; and comparing the dataset of the first rough gemstone with an existing dataset of a rough gemstone. Where the dataset of the first rough gemstone and the existing dataset match each other, the method comprises re-identifying the first rough gemstone as the same rough gemstone from which the existing dataset was obtained.

17 Claims, 9 Drawing Sheets

(51) Int. Cl.
*G06V 10/75* (2022.01)
*G06V 10/54* (2022.01)

(58) Field of Classification Search
CPC ...... G06V 10/46; G06V 10/54; G06V 10/758; G06V 20/647; G06K 9/00577; G06K 9/00208; G06K 9/6202; G06K 9/627; G06K 9/78
See application file for complete search history.

(56) References Cited

U.S. PATENT DOCUMENTS

| | | | |
|---|---|---|---|
| 2006/0066877 A1* | 3/2006 | Benzano | G06T 1/0007 356/603 |
| 2010/0250201 A1* | 9/2010 | Sivovolenko | G01N 21/87 703/1 |
| 2018/0137569 A1 | 5/2018 | Ariel et al. | |

FOREIGN PATENT DOCUMENTS

| | | |
|---|---|---|
| WO | 2006/117406 A2 | 11/2006 |
| WO | 2011/054822 A1 | 5/2011 |
| WO | 2016/092300 A1 | 6/2016 |

OTHER PUBLICATIONS

International Preliminary Report on Patentability for Application No. PCT/EP2020/064226, dated Dec. 30, 2021, 9 pages.
International Search Report and Written Opinion for Application No. PCT/EP2020/064226, dated Aug. 28, 2020, 14 pages.
Search Report for Application No. GB1908875.6 dated Nov. 15, 2019, 4 pages.
Keith Forbes, "Calibration, Recognition, and Shape from Silhouettes of Stones", Jun. 2007, The University of Cape Town, PhD Thesis, Department of Electrical Engineering, 257 pages.

* cited by examiner

RE-IDENTIFICATION OF ROUGH GEMSTONES

This application is a National Phase Application of International Patent Application No. PCT/EP2020/064226, filed on May 21, 2020, which is based on and claims priority to and benefits of British Patent Application GB 1908875.6, entitled "RE-IDENTIFICATION OF ROUGH GEMSTONES" and filed on Jun. 20, 2019. The entire content of all of the above identified applications is incorporated herein by reference.

TECHNICAL FIELD

The present invention relates to the re-identification of rough gemstones. Additionally, but not exclusively, the invention relates to the re-identification of rough diamonds.

BACKGROUND

Diamond ore is extracted from sites around the world utilising a range of methods, including open-pit, pipe and alluvial mining. Once recovered the ore may be crushed and then mixed with slurry to separate out the rough (i.e. uncut) diamonds, which are sorted into various categories, depending upon their quality: boart, industrial quality and gemstone quality. Boart is low quality diamond material that is often used in crushed form as an industrial abrasive. Industrial quality diamond may be used in drill bits, for example, while the highest quality stones are reserved to be cut and polished into faceted gemstones for use in jewellery, watches and the like.

There are many reasons why it is desirable to be able to track rough diamonds (or other gemstones) from the mine to the consumer, and even between consumers. Once a particular rough stone has been measured to determine its properties (e.g. shape, size, clarity, colour) it is desirable to store these measurements so that they do not need to be re-determined at a later stage of the stone's processing. Moreover, once a stone has been verified as genuine (i.e. non-synthetic, non-simulant), tracking the verified stone enables future owners—whether wholesalers, retailers or consumers—to have confidence in the value of the stone. This confidence facilitates transactions and valuations of the stone.

Additionally, tracking a rough diamond from the mine of origin confirms that the stone is not a "conflict diamond" or "blood diamond", defined by the Kimberley Process as a rough diamond "used to finance wars against governments". The Kimberley Process (KP) is an international certification scheme set up by the UN to ensure that every diamond export is accompanied by a KP certificate, and to prevent the import/export of diamonds from non-members of the scheme. The ability to accurately trace the origin of a rough diamond is therefore integral to the KP scheme.

In order to effectively and accurately track or trace an individual rough stone from the mine to a faceted gemstone cut from that rough stone, it is helpful to obtain information relating to the stone that will act as a unique "fingerprint". This fingerprint can be used to enable re-identification of the stone at a subsequent point in its journey.

SUMMARY

In one aspect of the present invention there is provided a method of re-identifying a rough gemstone. The method comprises providing a three-dimensional (3D) model of a first rough gemstone; generating a series of virtual two-dimensional (2D) silhouette images of the 3D model; processing each 2D image of the series of virtual 2D silhouette images to obtain a dataset associated with the first rough gemstone; and comparing the dataset of the first rough gemstone with an existing dataset of a rough gemstone. Where the dataset of the first rough gemstone and the existing dataset match each other, the method comprises re-identifying the first rough gemstone as the same rough gemstone from which the existing dataset was obtained.

The method may comprise capturing a virtual 2D silhouette image of the 3D model from each of a plurality of virtual viewpoints in a geodesic arrangement around the 3D model.

Processing each 2D image of the series of virtual 2D silhouette images may comprise converting each said 2D image into a set of geometric shapes that characterise a silhouette of the first rough gemstone present in said 2D image. The set of geometric shapes may be based upon one or more of a longest chord of the silhouette, an orthospread, and a convex hull deviance.

The dataset may comprise a series of numerical features derived from each of the 2D images of the series of virtual 2D silhouette images. The numerical features derived from each of the 2D images may comprise thirty-two features to which four statistical operations are applied.

The numerical features may include a measurement of one or more of blockiness, symmetry, normalised inverted longest chord, Hu's moments, orthonormal dispersion ratio, convex hull area ratio, standard convex hull deviance, normalised convex hull deviance, convex hull deviance ratio, normalised missing perimeter lengths, concave segment perimeter ratio, area and perimeter, longest chord, orthospread. The measurement may be obtained from one or more of the rough stone and the convex hull of the rough stone.

The method may comprise calculating one or more of the maximum, minimum, mean and coefficient of variance of each of the series of numerical features.

One or more of the dataset associated with the first rough gemstone, the existing dataset and a result of the comparison between the datasets may form part of a distributed ledger, such as a blockchain.

Providing the 3D model of the first rough gemstone may comprise obtaining a series of 2D silhouette images of the rough gemstone using one or more physical image capture devices and processing said series of 2D silhouette images to generate the 3D model of the rough stone. Said one or more physical image capture devices may be stationary while the series of 2D silhouette images are obtained.

The method may comprise illuminating the rough gemstone with collimated lighting while obtaining the series of 2D silhouette images.

The 3D model is optionally a surface model of the rough gemstone.

The method may comprise obtaining the existing dataset as part of a process of sorting the output of a mine. Re-identifying the rough gemstone may comprise confirming that the rough gemstone originated from that mine.

The rough gemstone is optionally a rough diamond.

The method may comprise comparing the dataset of the first rough gemstone with a plurality of existing datasets of rough gemstones stored in a database.

In another aspect of the present invention there is provided a method of confirming the mine of origin of a rough gemstone. The method comprises obtaining a first numerical dataset based upon geometric features in a series of 2D silhouette images of the rough gemstone, the first numerical dataset being obtained during a mine output sorting process; subsequently obtaining a second numerical dataset based upon geometric features in a further series of 2D silhouette images of the rough gemstone; and comparing the first and the second numerical datasets to confirm the mine of origin of the rough gemstone. The series of 2D silhouette images are obtained from a 3D model of the rough gemstone.

In a further aspect of the present invention there is provided a method of identifying a rough gemstone. The method comprises capturing a first series of 2D images of the rough gemstone; producing a 3D model of the rough gemstone from the first series of 2D images; generating a second series of 2D images of the 3D model, wherein the second series comprises virtual 2D images; and processing the second series of 2D images to obtain an identifier associated with the rough gemstone.

In a still further aspect of the present invention there is provided an apparatus for obtaining an identifier associated with a rough gemstone. The apparatus comprises one or more image capture devices configured to obtain a first series of 2D silhouette images of the rough stone from a plurality of viewpoints; and a processor configured to produce a 3D model of the rough stone from the first series of 2D silhouette images; generate a second series of virtual 2D silhouette images from the 3D model; and process the second series of virtual 2D silhouette images to obtain an identifier associated with the rough gemstone.

DETAILED DESCRIPTION

Described herein with reference to FIGS. 1 to 13 is a method of re-identifying rough gemstones. In one example, the method comprises providing a 3D model of a first rough gemstone; generating a series of virtual 2D silhouette images of the 3D model; processing each 2D image of the series of virtual 2D silhouette images to obtain a dataset associated with the first rough gemstone; and comparing the dataset of the first rough gemstone with an existing dataset of a rough gemstone. Where the dataset of the first rough gemstone and the existing dataset match each other, the first rough gemstone may be re-identified as the same rough gemstone from which the existing dataset was obtained.

In its simplest form, a dataset associated with a rough gemstone may comprise a sequence of numbers. In one example, each number may represent one of the 128 features described below. The number of features may increase, if other properties of the gemstone are introduced, or may decrease, if certain properties are not useful in distinguishing one stone from another. Alternatively or additionally, the dataset may include other data, such as the 3D model, colour, weight, quality of the rough gemstone. In one non-limiting example, the dataset may include the original 2D images of the rough gemstone.

Also described herein is a method of confirming the mine of origin of a rough gemstone. In one example, the method comprises obtaining a first numerical dataset based upon geometric features in a series of 2D silhouette images of the rough gemstone, the first numerical dataset being obtained during a mine output sorting process; subsequently obtaining a second numerical dataset based upon geometric features in a further series of 2D silhouette images of the rough gemstone; and comparing the first and the second numerical datasets to confirm the mine of origin of the rough gemstone. The series of 2D silhouette images are obtained from a 3D model of the rough gemstone.

Further described is a method of identifying a rough gemstone. In one example, the method comprises capturing a first series of 2D images of the rough gemstone, producing a 3D model of the rough gemstone from the series of 2D images, generating a second series of 2D images of the 3D model, wherein the second series comprises virtual 2D images, and processing the second series of 2D images to obtain an identifier associated with the rough gemstone.

Also described herein is an exemplary apparatus for carrying out at least some of the steps of the above-described methods.

Figure 1:
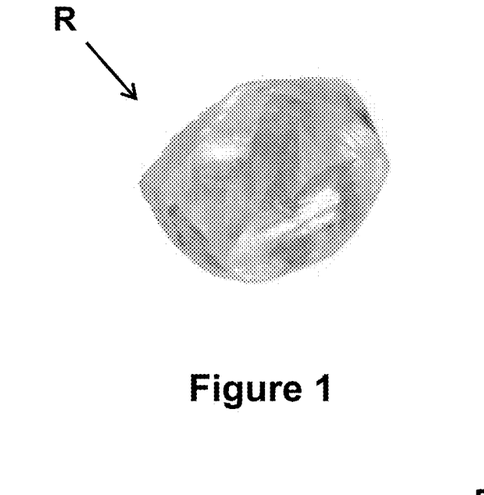
FIG. 1 is a perspective view of a rough diamond.

In order to obtain information which can be subsequently used to re-identify a rough stone, such as the stone R illustrated in FIG. 1, the method may initially comprise obtaining a series of 2D silhouette, or surface, images of the rough stone. These images include the outline or shape of the stone's surface.

Figure 2A:
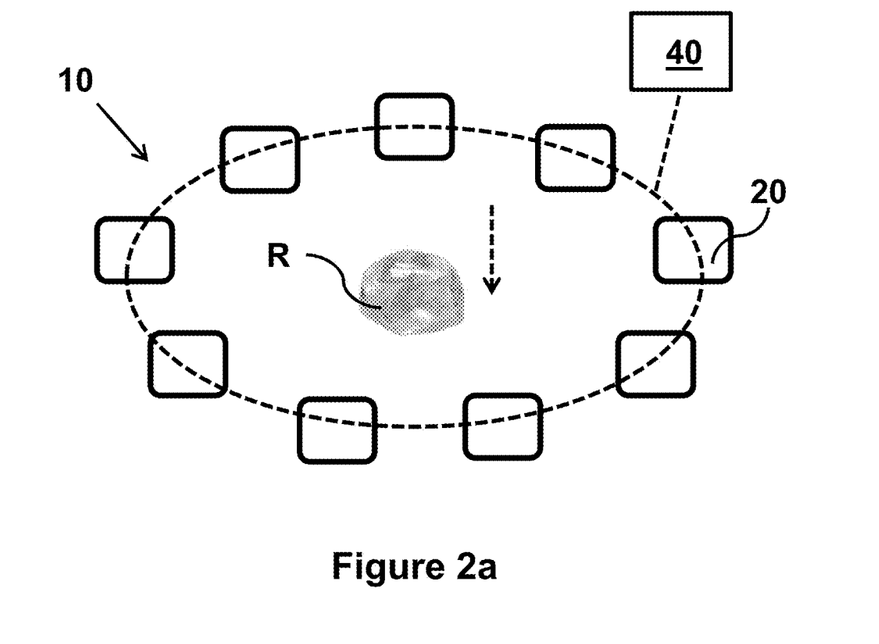
FIG. 2*a* is a schematic illustrating an exemplary apparatus for obtaining 2D silhouette images of a rough stone.

As illustrated in FIG. 2*a*, an exemplary apparatus 10 for carrying out this step includes nine image capture devices 20 (e.g. cameras), arranged substantially in a circle, and one or more light sources (not shown). The image capture devices 20 are configured to obtain images of a rough stone R dropped through the centre of the circle, such that it passes in freefall past the image capture devices 20, which are substantially co-planar with one another. As the stone R freefalls past the image capture devices 20, each device 20 simultaneously captures one or more 2D images of the stone R from different viewpoints. In one example, illustrated in FIG. 2*b*, each image capture device 20 has its own light source 22 which is positioned radially opposite the image capture device 20, and there is always an odd number of image capture devices 20, so that no image capture device 20 is opposite another.

Figure 3:
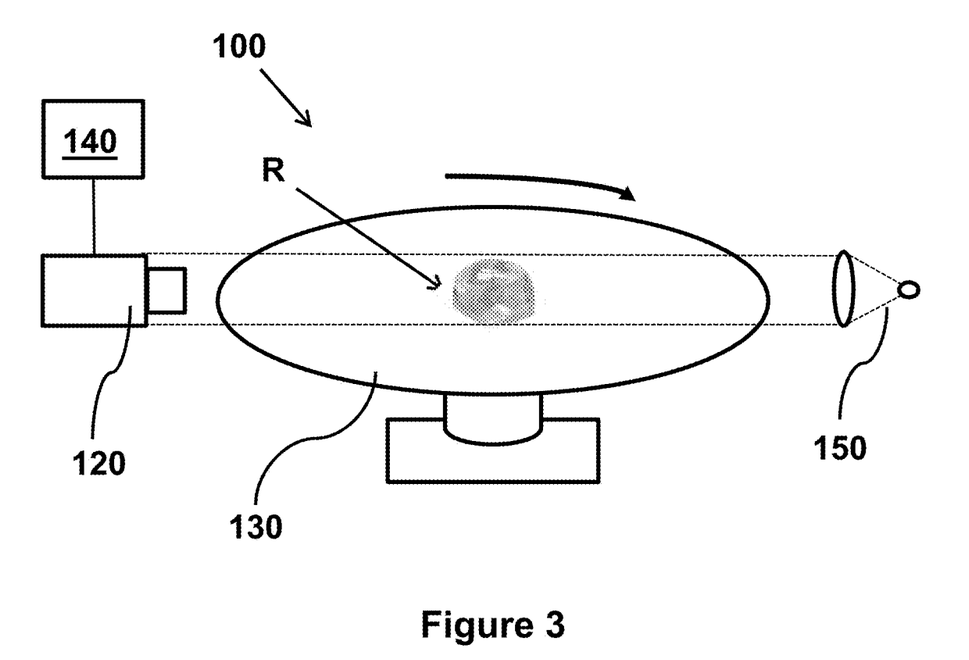
FIG. 3 is a schematic illustrating an alternative exemplary apparatus for obtaining 2D silhouette images of a rough stone.

In an alternative exemplary apparatus 100, illustrated in FIG. 3, a single image capture device 120 and a turntable 130 may be used to capture the 2D surface images of the stone R. In this example, the stone R is placed on an upper surface of the turntable 130 and a sequence of 2D surface images of the rough stone R is obtained by the image capture device 120 as the turntable 130 rotates through a series of discrete rotational increments. For example, the image capture device 120 may obtain a 2D image of the rough stone R at rotational increments of 40°, i.e. nine images in a complete rotation of the turntable 130. Alternatively or additionally, more than one image capture device may be used to capture 2D images of the stone as it rotates.

In each case, it is preferable to obtain 2D surface or silhouette images of the rough stone under collimated lighting conditions, for example using a laser light source 150, as shown in FIG. 3. Where a single image capture device 120 is used the collimated light source 150 may be located on an opposite side of the stone R to the image capture device 120.

Figure 2B:
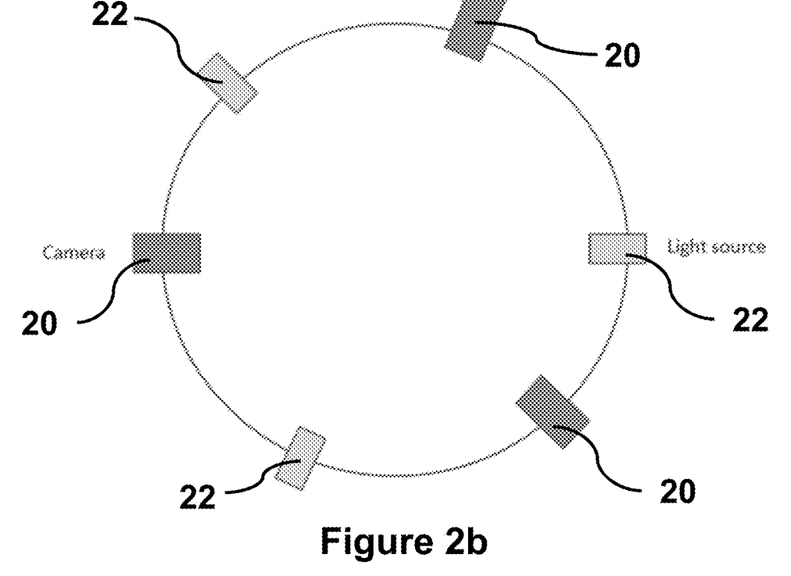
FIG. 2*b* is a schematic illustrating a further exemplary apparatus for obtaining 2D silhouette images of a rough stone.

The exemplary apparatus 10, 100 described above may further comprise a processor 40, 140, to which the captured 2D surface images of the rough stone R are transferred. The processor 40, 140 may be collocated with or remote from the image capture devices 20, 120 and may further be associated with a collocated or remote storage device, onto which the captured images are stored (not shown here). The processor 40, 140 may form part of a computer system (not shown), such as a desktop, laptop, tablet PC or other processing device.

The processor combines or otherwise processes the series or sequence of 2D surface images of the rough stone to produce a virtual 3D model of the surface of the stone. Methods of converting a number of 2D images into a 3D model comprised of the 2D images, such as the visual hull approach, are known. The generated 3D model of the surface of the rough stone may be stored on the associated storage device.

Once the 3D model of the rough stone has been generated by the processor, a series of virtual 2D images of the 3D model is obtained using virtual image capture devices "positioned" around the 3D virtual representation of the rough stone. In other words, a virtual 2D silhouette image of the 3D model is captured from each of a plurality of virtual viewpoints. The viewpoints, or virtual image capture devices, are preferably arranged evenly around the virtual stone, for example, in a geodesic pattern. The series of virtual 2D images may be generated from the 3D model using the same processor, or may be generated separately by a different processor.

Figure 4:
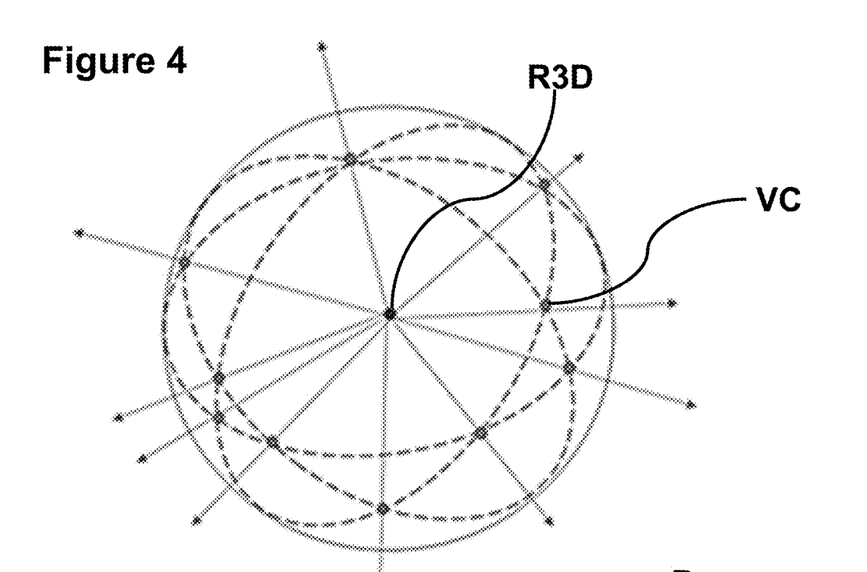
FIG. 4 illustrates a plurality of virtual image capture devices in a geodesic arrangement around a 3D model of a rough stone.

FIG. 4 illustrates a virtual 3D model R3D of a rough stone "surrounded" by virtual image capture devices VC "positioned" in a geodesic arrangement around the 3D model R3D. In this example, ten such virtual image capture devices VC are illustrated, but it will be appreciated that a greater or smaller number of virtual viewpoints may be selected. The number of virtual image captures devices VC need not be the same as the number of physical image capture devices 20, 120 previously used to obtain the series of 2D surface images of the real rough stone.

Figure 5:
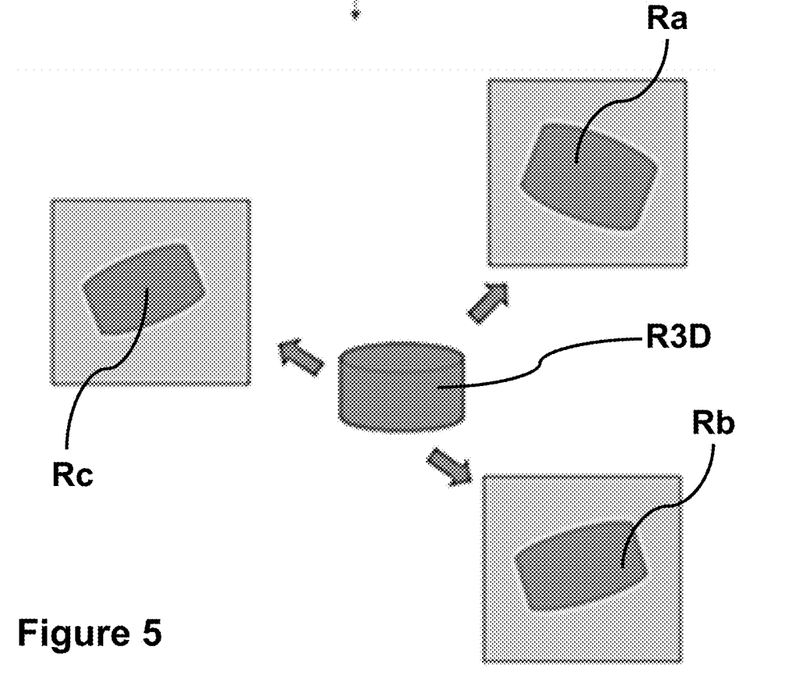
FIG. 5 illustrates a series of 2D silhouette images of the 3D model obtained by the virtual image capture devices.

As shown in FIG. 5, the virtual image capture devices capture a number of 2D images Ra, Rb, Rc of the 3D model R3D of the rough stone (which is illustrated here as a cylinder for simplicity). The series of 2D images may be surface, or silhouette, images. Although three 2D images Ra, Rb, Rc are illustrated here, it will be understood that a greater or smaller number of 2D images may be obtained by the virtual image capture devices, from a range of different viewpoints.

As a result of the even (e.g. geodesic) arrangement of the virtual image capture devices around the 3D model of the rough stone, the 2D images generated by the virtual image capture devices are not biased towards any particular plane. This may not be true of the physical image capture devices 20, 120 illustrated in FIGS. 2 and 3, which will tend to be biased towards a plane that is generally orthogonal to the direction of travel of the rough stone R in freefall, in the case of the apparatus 10 of FIG. 2; or generally parallel to the upper surface of the turntable 130, in the case of the apparatus 20 of FIG. 3. Thus, the "real" or "raw" 2D silhouette images of the rough stone R captured by the physical image capture devices 20, 120 may also be biased towards the plane direction.

In contrast, by projecting the 3D model of the rough stone into "virtual views" of virtual image capture devices, and by distributing these virtual devices evenly in a spherical space around the 3D model, it is ensured that information regarding the rough stone obtained from the virtual 2D surface images is truly independent of the orientation of the physical image capture devices and the rough stone itself.

Figure 6:
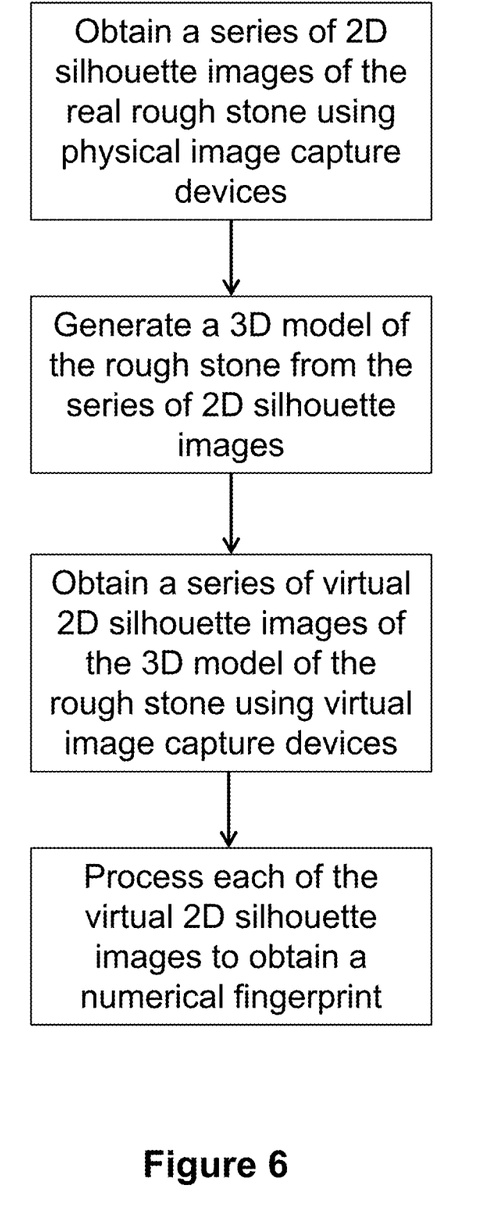
FIG. 6 illustrates a method of obtaining a numerical fingerprint of a rough stone.

FIG. 6 illustrates an exemplary method of obtaining a dataset associated with a rough stone, the dataset providing a numerical "fingerprint" of, or "score" for, the stone. In this respect, as discussed above, the dataset, fingerprint or score can be regarded as an identifier for the stone. In this example, a series of 2D silhouette images of the real (i.e. physical) rough stone are obtained using physical image capture devices, such as cameras. These images may, for example, be obtained by the apparatus described with reference to FIG. 2a, 2b or 3. A 3D model of the rough stone is then generated from the series of 2D silhouette images. A series of virtual 2D silhouette images is obtained from the 3D model, as described with reference to FIGS. 4 and 5. Each of the virtual 2D silhouette images is then processed to obtain a numerical dataset, or fingerprint. The fingerprint for each 2D silhouette image may be combined to produce an overall numerical fingerprint, or dataset, for the rough stone.

Of course, it will be appreciated that a series of virtual 2D silhouette images may be generated from virtual image capture devices, as described above, from a 3D model of a rough stone where the 3D model is pre-existing and/or has been produced elsewhere. In this case, the steps of obtaining a series of real 2D silhouette images from the real rough stone, and the generation of the 3D model, may already have been completed.

An exemplary method of processing the virtual 2D images to obtain a fingerprint which will allow re-identification of a rough stone will now be described. The fingerprint, or score, corresponding to an individual rough gemstone is based upon a number of pre-determined measurements and calculations carried out by a processor. Once obtained from a rough stone, this fingerprint can be stored or otherwise associated with the rough stone, and can be referred to in the future to determine or confirm the rough stone's identity.

If obtained at or close to the point of extraction from the mine, this numerical fingerprint may be used to trace the stone's origin (i.e. to confirm that the rough gemstone originated from a particular mine). For example, the fingerprint or dataset may be obtained as part of a process of sorting the output of a mine.

Storage of the data associated with the fingerprint may be accomplished using various blockchain technologies, for example, which enable re-verification of a stone's identity at the point of each transaction in the chain. In this respect, the data may form part of a block within a growing blockchain that comprises a time-stamped distributed ledger.

Each block of the chain is independently verifiable and secured using cryptographic authentication and time stamping.

The data associated with the fingerprint (i.e. the identifier of the stone) may be stored in a database. Fingerprints for a plurality of rough stones may be so stored, and a generated numerical fingerprint may be compared with the plurality of fingerprints stored in the database to establish whether there is a match. Similarly, two or more already-stored fingerprints may be compared with one another, such that generating a new fingerprint is not required.

In one exemplary method, the fingerprint of the stone is obtained as follows. This method comprises the generation of 128 features relating to the rough stone, however, as discussed above, the number of features utilised may increase, if other properties of the gemstone are introduced, or may decrease, if certain properties are not useful in distinguishing one stone from another.

In this exemplary method, from each of the virtual 2D surface or silhouette images obtained by the virtual image capture devices an initial thirty-two numerical features are generated of the rough stone in the 3D model. Four statistical operations are then applied across all of the virtual 2D images, so that four statistical values are generated for each of the initial thirty-two features, resulting in a total of 128 features associated with the rough stone. These operations will be discussed in more detail below.

Figure 7:
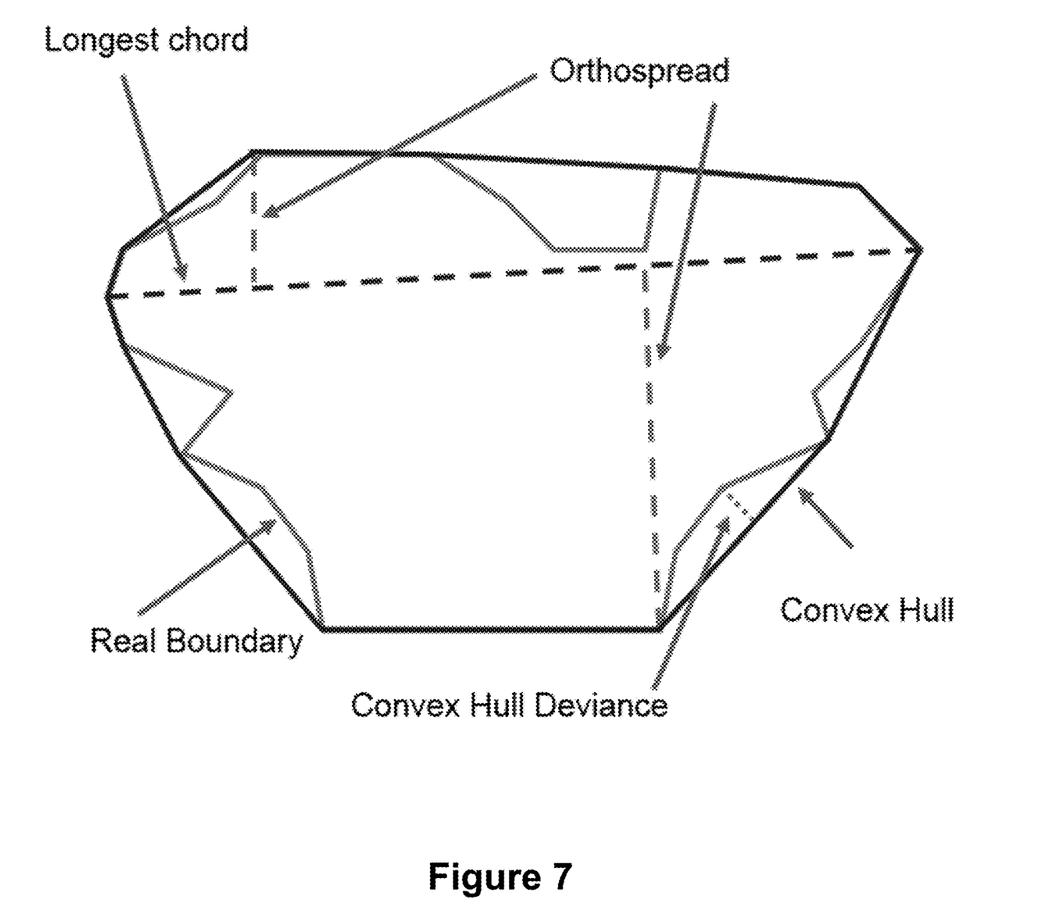
FIG. 7 illustrates exemplary geometric shapes and features of a silhouette image of a rough stone.

Before generating the initial thirty-two numerical features, it is necessary to convert each of the virtual 2D silhouette images captured by the virtual image capture devices into a set of geometric shapes or features. These geometric shapes or features characterise the silhouette or outline of the rough stone as illustrated in each respective virtual 2D image. Exemplary geometric shapes and features are shown in FIG. 7; these shapes are formed by considering, for example, one or more of: the longest chord of the silhouette, the orthospread, and the convex hull deviance.

The convex hull of a 2D silhouette image is defined as the smallest convex polygon into which the real silhouette of the rough stone (i.e. the real object) will fit. Since the polygon must be convex there can be no inwardly directed vertices. As illustrated in FIG. 7, the area within the convex hull of a particular 2D silhouette is typically larger in area than the area within the boundary of that 2D silhouette of the stone. The convex hull deviance, as illustrated in FIG. 7, is a difference between the real boundary of the silhouette, as it appears in the virtual 2D image, and the geometric convex hull.

Figure 8:
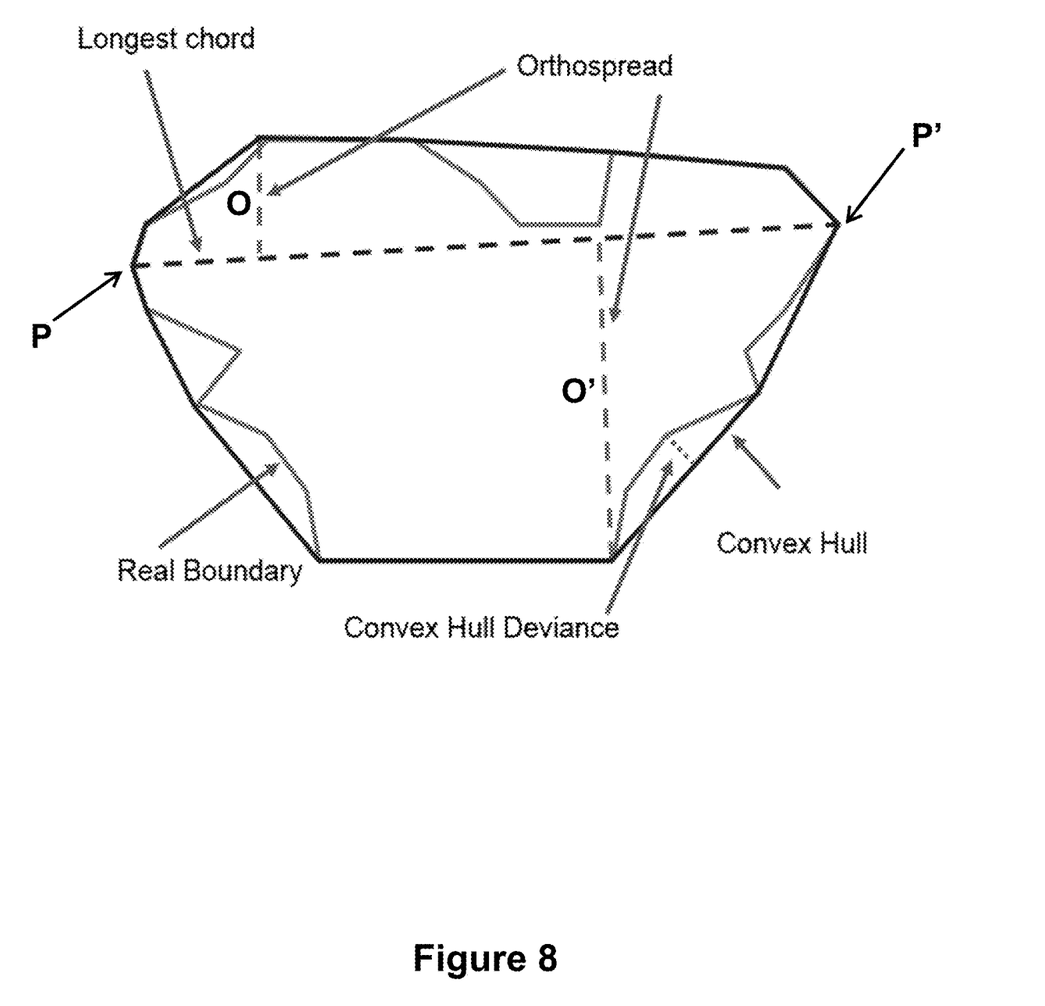
FIG. 8 illustrates further exemplary geometric shapes and features of the silhouette image of the rough stone.

The longest chord, as illustrated in FIG. 8, is the longest distance for any two points on the boundary of the convex hull polygon. In the illustrated example of FIG. 8, the longest chord is the line between points P and P'.

Once the longest chord is found, it separates the boundary of the stone's outline into two parts, one on each side of the chord. Each point on the boundary has an orthogonal distance to the chord. On each side of the longest chord is one point that has the longest orthogonal distance to the longest chord. Because there are two sides, there are two longest orthogonal distances. In the example of FIG. 8, these two distances are the lines represented by O and O'. The sum of these two longest orthogonal distances, e.g. O+O', is defined as the orthospread.

In this exemplary method, the initial thirty-two features generated from each virtual 2D silhouette image of the rough stone can be enumerated as follows. It will be appreciated, however, that additional or alternative features may be generated from the 2D silhouette images:

1. Blockiness Measurement
2. Symmetry
3. Normalised Inverted Longest Chord
4. Hu's Moments—calculated from the real object ($M_1$)
5. Hu's Moments—calculated from the real object ($M_2$)
6. Hu's Moments—calculated from the real object ($M_3$)
7. Hu's Moments—calculated from the real object ($M_4$)
8. Hu's Moments—calculated from the convex hull ($M_1$)
9. Hu's Moments—calculated from the convex hull ($M_2$)
10. Hu's Moments—calculated from the convex hull ($M_3$)
11. Hu's Moments—calculated from the convex hull ($M_4$)
12. Orthonormal Dispersion Ratio (real boundary)
13. Orthonormal Dispersion Ratio (convex hull)
14. Convex Hull Area Ratio
15. Standard Convex Hull Deviance
16. Normalised Convex Hull Deviance 1
17. Normalised Convex Hull Deviance 3
18. Convex Hull Deviance Ratio 1
19. Convex Hull Deviance Ratio 2
20. Convex Hull Deviance Ratio 5
21. Convex Hull Deviance Ratio 3
22. Convex Hull Deviance Ratio 4
23. Convex Hull Deviance Ratio 6
24. Normalised Missing Perimeter Lengths 1
25. Normalised Missing Perimeter Lengths 2
26. Concave Segment Perimeter Ratio
27. Area of the Real Object
28. Perimeter of the Real Object
29. Area of the Convex Hull
30. Perimeter of the Convex Hull
31. Longest Chord
32. Orthospread Each of the above 32 exemplary features will now be discussed in greater detail. It will be appreciated that the term "real object" in the description that follows refers to the rough stone as imaged in a particular virtual 2D silhouette image, generated from the 3D model of the rough stone.

1. Blockiness Measurement

The blockiness measurement is defined as the ratio of the real object area over the square of the real object perimeter:

$$\frac{4\pi Area}{Perimeter^2}$$

For a circle, the above equation would give a value of 1. For a very long and thin object, the value is close to 0. Any other shapes will have a value between 0 and 1.

2. Symmetry

Figure 9:
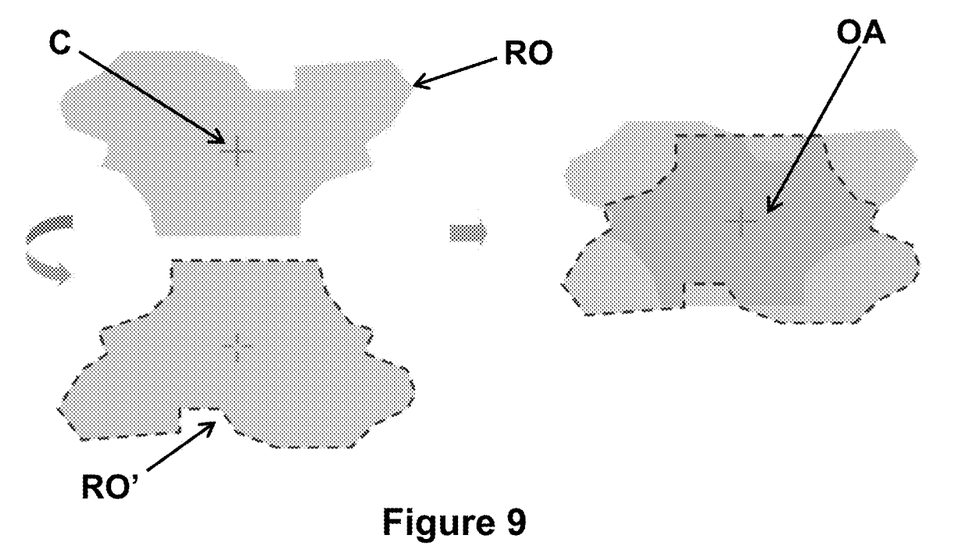
FIG. 9 is a schematic which illustrates an overlap region between a silhouette image of a rough stone and the same image, rotated around its centroid.

The symmetry measurement comprises finding the centroid C (i.e. the geometric centre) of the real object RO, rotating the object RO around the centroid C by 180 degrees, then aligning the original RO and the rotated RO' real objects by their centroids C, as illustrated in FIG. 9. The symmetry measurement is then defined as the ratio of the area of overlap OA between the superimposed original real object RO and the rotated real object RO' (when the centroids C are aligned) and the area of the real object RO:

$$\frac{Overlapped\ Area}{Area}$$

3. Normalised Inverted Longest Chord

The normalised inverted longest chord is the aspect ratio of the real object, as defined below:

$$\frac{Orthospread}{Longest\ Chord}$$

4-7. Hu's Moments—Calculated from the Real Object

Hu's moments are a set of seven numbers which are calculated using central moments that are invariant to transformations (e.g. translation, scale, rotation). Calculation of the moments enables the extraction of a shape feature vector which represents the shape of the real object.

Calculated from the real object, Hu's moments are determined as follows:

First calculate the central moments:

$$m_{pq} = \sum_{xy} x^p y^q$$

The real object centroid (co-ordinates $x_c$, $y_c$) is given as:

$$x_c = \frac{m_{10}}{m_{00}},$$

$$y_c = \frac{m_{01}}{m_{00}}$$

Then calculate the following values, which represent the seven Hu's moments:

$$\mu_{11} = \frac{1}{m_{00}}\left(m_{11} - \frac{m_{10}m_{01}}{m_{00}}\right)$$

$$\mu_{20} = \frac{1}{m_{00}}\left(m_{20} - \frac{m_{10}^2}{m_{00}}\right)$$

$$\mu_{02} = \frac{1}{m_{00}}\left(m_{02} - \frac{m_{01}^2}{m_{00}}\right)$$

$$\mu_{12} = \frac{1}{m_{00}}\left(m_{12} - 2m_{11}y_c - m_{02}x_c + 2m_{10}y_c^2\right)$$

$$\mu_{21} = \frac{1}{m_{00}}\left(m_{21} - 2m_{11}x_c - m_{20}y_c + 2m_{01}x_c^2\right)$$

$$\mu_{30} = \frac{1}{m_{00}}\left(m_{30} - 3m_{20}x_c + 2m_{10}x_c^2\right)$$

$$\mu_{03} = \frac{1}{m_{00}}\left(m_{03} - 3m_{02}y_c + 2m_{01}y_c^2\right)$$

This then leads to:

$$N_1 = \mu_{20} + \mu_{02}$$

$$N_2 = (\mu_{20} - \mu_{02})^2 + 4\mu_{11}^2$$

$$N_3 = (\mu_{30} - 3\mu_{12})^2 + (3\mu_{21} - \mu_{03})^2$$

$$N_4 = (\mu_{30} + \mu_{12})^2 + (\mu_{21} + \mu_{03})^2$$

Where $N_1$ to $N_4$ are intermediate results.

Finally, the first four of the seven Hu's moments are used (the first four are useful in showing differences between two images):

$$M_1 = \frac{N_1}{m_{00}}$$

$$M_2 = \frac{\sqrt{N_2}}{N_1}$$

$$M_3 = \frac{\sqrt[3]{N_3}}{N_1}$$

$$M_4 = \frac{\sqrt[3]{N_4}}{N_1}$$

8-11. Hu's Moments—Calculated from the Convex Hull

Hu's seven moments can also be calculated using the convex hull instead of the real object. Two sets of four moments can therefore be calculated, relating to the real object and the convex hull, as shown above.

12-13. Orthonormal Dispersion Ratio

The orthonormal dispersion ratio (real boundary and convex hull) is determined using the intermediate moments calculated above ($\mu_{02}$, $\mu_{11}$, $\mu_{20}$). From these moments, obtain the following matrix:

$$\begin{bmatrix} a & b \\ c & d \end{bmatrix} = \begin{bmatrix} \mu_{20} & \mu_{11} \\ \mu_{11} & \mu_{02} \end{bmatrix}$$

The eigenvalues of this matrix are:

$$u = \frac{1}{2}\left[a + c + \sqrt{(a+c)^2 + 4(b^2 - ac)}\right]$$

$$v = \frac{1}{2}\left[a + c - \sqrt{(a+c)^2 + 4(b^2 - ac)}\right]$$

The orthonormal dispersion ratio is then given as:

$$\sqrt{\frac{v}{u}}$$

The orthonormal dispersion ratio is another way to measure the aspect ratio of the rough stone. This ratio may be calculated using both the real object boundary and the convex hull.

14. Convex Hull Area Ratio

The convex hull area ratio is simply the ratio of the real object area and the convex hull area.

15. Standard Convex Hull Deviance

Figure 10:
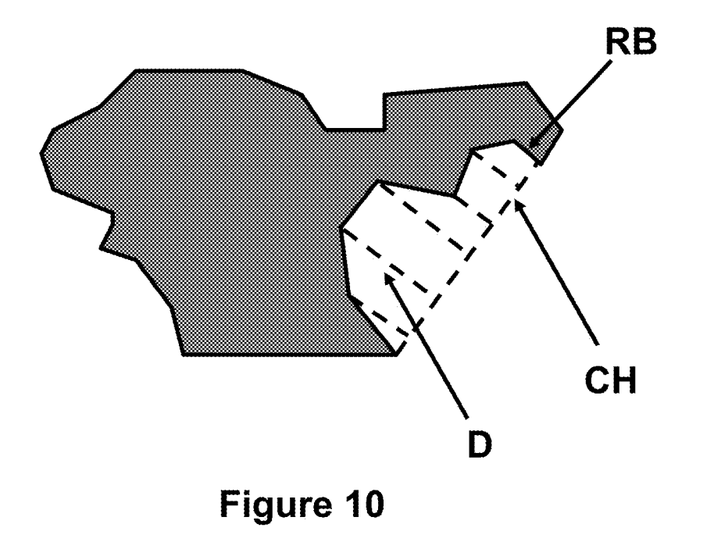
FIG. 10 illustrates a deviance between a concave point on a boundary of the rough stone and its convex hull.

As illustrated in FIG. 10 a deviance D is a distance from a concave point on the real object boundary RB to the convex hull CH.

The standard convex hull deviance is the maximum of such deviances i.e. the longest distance between a concave point on the real object boundary and the convex hull.

Each deviance may be normalised by dividing each deviance value by the distance between the relevant concave point and the real object centroid.

16. Normalised Convex Hull Deviance 1

The normalised convex hull deviance 1 is the maximum of the normalised deviances.

17. Normalised Convex Hull Deviance 3

The normalised convex hull deviance 3 is found by dividing the standard convex hull deviance by the square root of the real object area.

18. Convex Hull Deviance Ratio 1

In this example, the convex hull deviance ratio 1 is found by dividing the standard convex hull deviance by the convex hull perimeter.

19. Convex Hull Deviance Ratio 2

In this example, the convex hull deviance ratio 2 is found by dividing the standard convex hull deviance by the square root of the convex hull area.

20. Convex Hull Deviance Ratio 5

In this example, the convex hull deviance ratio 5 is found by dividing the standard convex hull deviance by the orthospread value.

21. Convex Hull Deviance Ratio 3

In this example, the convex hull deviance ratio 3 is the average of the deviances divided by the convex hull perimeter.

22. Convex Hull Deviance Ratio 4

In this example, the convex hull deviance ratio 4 is the average of the deviances divided by the square root of the convex hull area.

23. Convex Hull Deviance Ratio 6

In this example, the convex hull deviance ratio 6 is the average of the deviances divided by the orthospread value.

24-25. Normalised Missing Perimeter Lengths 1 and 2

Figure 11:
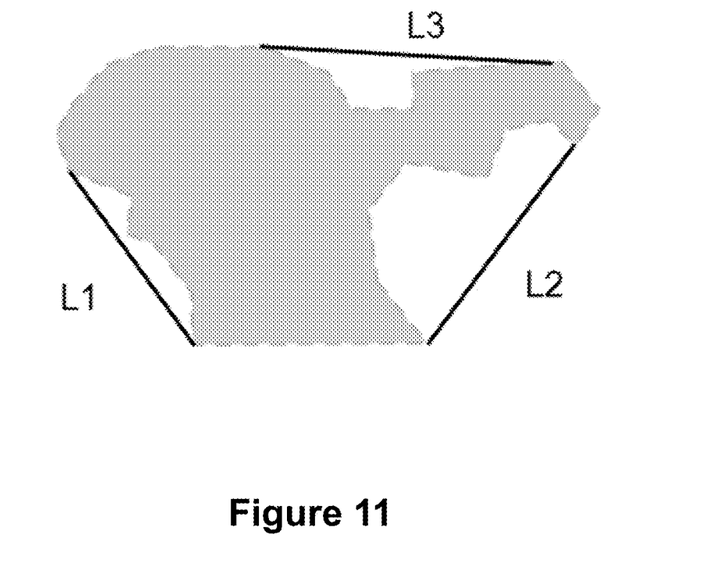
FIG. 11 illustrates missing perimeter lengths of the rough stone perimeter.

As illustrated in FIG. 11, in this example the normalised missing perimeter lengths 1 and 2 are determined by finding the concave segments of the real object perimeter and their corresponding convex vectors L1, L2, L3 . . . . The sum of these convex vectors is then calculated (i.e. L1+L2+L3+ . . . ).

Normalise (i.e. divide) the sum of the convex vectors with the real perimeter of the real object, thus giving the normalised missing perimeter lengths 1.

Normalise the sum of the convex vectors with the convex hull perimeter, thus giving the normalised missing perimeter lengths 2.

26. Concave Segment Perimeter Ratio

Figure 12:
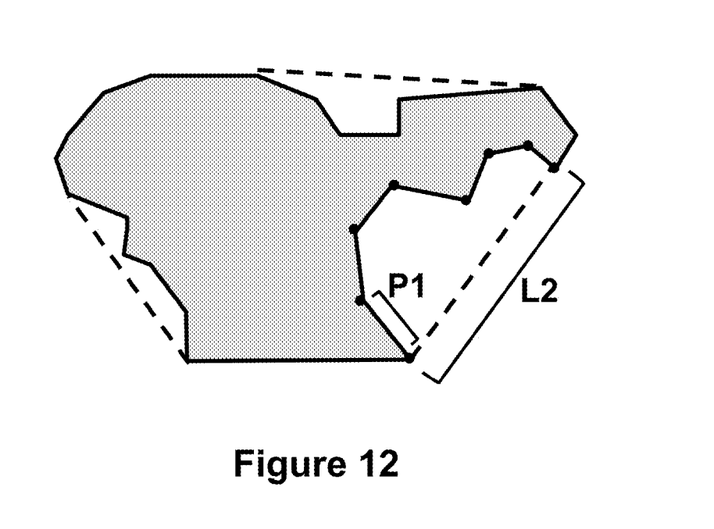
FIG. 12 illustrates a degree of concavity of the perimeter of the rough stone.

As shown in FIG. 12, the concave segment perimeter ratio can be calculated by determining the partial perimeter P1 of a concave segment of the real object (i.e. a partial perimeter joining concave points) and its corresponding convex segment L2 (i.e. a partial perimeter joining convex points). This calculation is applied to all partial perimeters joining convex points.

The ratio of L2/P1 indicates the degree of the concavity of the perimeter of the real object. Repeat the above process for all concave segments of the real object and determine the minimum L2/P1 ratio. This minimum L2/P1 ratio is the concave segment perimeter ratio.

27-32. The Remaining Exemplary Geometric Features of the Rough Stone Comprise:

The area of the real object (i.e. the area of the silhouette)
The perimeter of the real object (i.e. the perimeter of the silhouette)
The area of the convex hull
The perimeter of the convex hull
The longest chord (as described with reference to FIG. 8)
The orthospread (as described with reference to FIGS. 7 and 8)

As discussed in the above example, from each of the virtual 2D surface or silhouette images obtained by the virtual image capture devices, thirty-two features are generated of the rough stone in the 3D model. As described below, four statistical operations are then applied to each of the virtual 2D images, so that four statistical values are generated for each of the thirty-two features, resulting in a total of 128 features associated with the rough stone.

In one non-limiting example, there may be $N_I$ virtual 2D images of the rough stone. In the exemplary method described above, each virtual 2D image produces thirty-two features. For each of the thirty-two features, there are $N_V$ corresponding values coming out of the $N_I$ images. Four statistical operations are applied to these $N_V$ values, so that four values (minimum, mean, maximum, and coefficient of variance) are obtained for each feature once the data is combined. The coefficient of variance is defined herein as the standard deviation divided by the mean.

A total of 32×4=128 features are generated, once all features are statistically combined. Regardless of how many images of the rough stone are obtained (that is, regardless of the number of images $N_I$), in this exemplary method the result is always 128 features.

For example, the number of virtual 2D images obtained from the 3D model of the rough stone may equal 150 (i.e. $N_I$=150). To obtain 150 images, there may be 150 different virtual camera views in the geodesic arrangement. The number of images may be more or less than 150; in general it is desirable for $N_I$ to be a large number.

From each of the 150 virtual 2D images, 32 features of the stone are generated (based upon the exemplary method above). Then, for each feature of the 32 features, the four statistical operations are applied, e.g. from the 150 values for the blockiness measurement (feature 1 above), the minimum value of the 150 values, maximum value of the 150 values, mean and coefficient of variance of the 150 values are calculated.

This produces four values for the overall blockiness measurement. The same statistical operations are carried out for the remaining 31 features, such that there are four values for each of the 32 features i.e. 128 values/features in total.

Because the virtual 2D views may be obtained using a geodesic arrangement, as discussed above, the four statistical operations remove the orientation factor, so that a fingerprint of the rough stone is generated independent of its orientation.

These exemplary 128 features can be used to re-identify a rough stone, providing a unique fingerprint, or score. There may be some redundancy between the 128 features, in which case they may not all be necessary for re-identification. Alternatively or additionally, further processing may be carried out to reduce the 128 features to a smaller number (for example, using Fisher linear discriminant analysis).

In further examples, not discussed here, a subset of the above-described 32 features may be selected. For example, 5 of the above 32 features may be selected and used to generate the fingerprint of a rough stone. In alternative examples, 2 or 10 features of the above 32 features may provide an acceptable fingerprint, capable of re-identifying a rough stone or of distinguishing one rough stone from another. Alternatively, a subset of the above 32 features may be utilised in combination with other features not disclosed herein to generate a fingerprint of a rough stone.

It will be appreciated that the fingerprint described herein may be used to re-identify a rough stone and/or a virtual 3D model of a rough stone. In this respect, the physical rough stone need not be present for re-identification to take place.

For the purposes of re-identification, a first fingerprint or score may be calculated (for example, as outlined in the exemplary method described above) for a physical rough stone, or a 3D model of a rough stone, and this first numerical fingerprint may be compared to a second, previously-obtained numerical fingerprint. The second fingerprint may be retrieved from storage in a database, for example. If there is a match between the first and second fingerprints, then the rough stone can be positively re-identified as the same stone from which the second fingerprint was previously obtained. Any measured properties of the rough stone from which the second fingerprint was obtained (e.g. shape, size, carat, clarity, colour, type, treatment, chemical composition, light performance) may therefore be associated with the rough stone from which the first fingerprint or score was obtained. Alternatively or additionally, the mine of origin of the rough stone from which the first fingerprint or score was obtained may be confirmed. Alternatively or additionally, previous transactions and/or locations associated with the rough stone from which the first fingerprint or score was obtained may be obtained and/or tracked.

In one non-limiting example, the comparison of the two fingerprints may be carried out as follows. Assuming that 128 features are generated, as described in the example above, each feature vector may be assumed to be a point in 128-dimensional space. The distance between two feature vectors from two rough stones may be measured. If this distance is below a certain threshold, then the two rough stones are accepted as a match i.e. they are the same stone.

The comparison of the first and second (new and old) numerical fingerprints may be carried out in an automated fashion by a processor, for example, using an algorithm. The comparison may form part of one or more blockchain operations. Alternatively or additionally, whether the two fingerprints match or not may be evaluated by a user.

The obtaining of (for example) thirty-two exemplary features for each 2D silhouette image, and the application of four statistical operations to each of the thirty-two features, provides a highly complex and detailed dataset (i.e. a fingerprint, or score) and enables re-identification of the rough stone (or a 3D model thereof) with a high degree of accuracy and confidence.

It will be understood that the above exemplary method of re-identification of a rough stone comprises the comparison of a numerical fingerprint with another numerical fingerprint, or with multiple numerical fingerprints (i.e. identifiers) rather than the comparison of 2D or 3D images with other 2D or 3D images. The numerical fingerprint is derived from calculated properties of the 2D images, rather than directly from the 2D images themselves, although the 2D images may form part of the dataset as discussed above. The numerical fingerprints may be stored in a database to facilitate comparison.

Moreover, the numerical fingerprint is derived from the properties of 2D silhouette images obtained by virtual image capture devices, and not from the physical stone itself. As previously discussed, the 2D images generated by virtual image capture devices are not biased towards any particular plane, unlike the physical image capture devices. The accuracy of the identification of the stone is therefore improved.

Further, a rough gemstone may be positively identified by the direct comparison of numerical fingerprints. For the purposes of re-identification, the need to obtain chemical samples or to measure chemical properties of a rough gemstone is therefore obviated.

Figure 13:
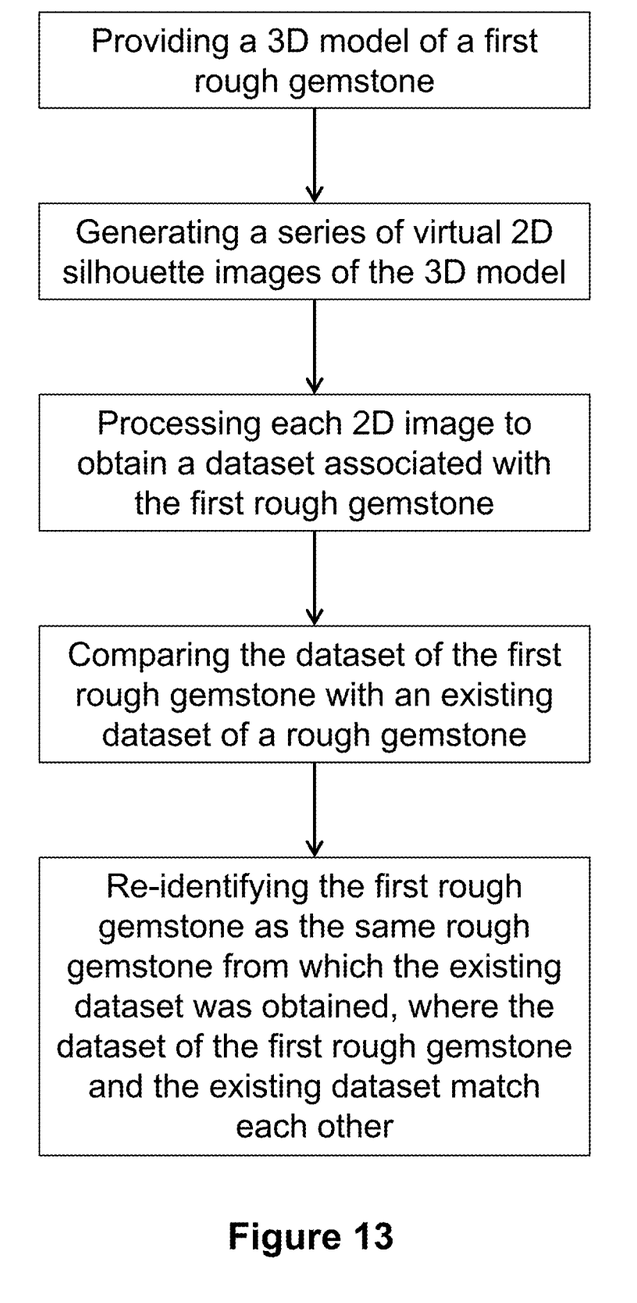
FIG. 13 illustrates a method of re-identifying a rough gemstone.

FIG. 13 illustrates a method of generating a dataset, or fingerprint, which can be used to re-identify a rough gemstone, such as a diamond. The method comprises the steps of:
S1: providing a 3D model of a first rough gemstone;
S2: generating a series of virtual 2D silhouette images of the 3D model;
S3: processing each 2D image of the series of virtual 2D silhouette images to obtain a dataset associated with the first rough gemstone;
S4: comparing the dataset of the first rough gemstone with an existing dataset of a rough gemstone; and
S5: where the dataset of the first rough gemstone and the existing dataset match each other, re-identifying the first rough gemstone as the same rough gemstone from which the existing dataset was obtained.

As previously discussed, the initial identification of the rough gemstone, i.e. the generation of the existing dataset, may be carried out via the following steps: (i) capturing a first series of 2D images of the rough gemstone; (ii) producing a 3D model of the rough gemstone from the series of 2D images; (iii) generating a second series of 2D images of the 3D model, wherein the second series comprises virtual 2D images; and (iv) processing the second series of 2D images to obtain an identifier associated with the rough gemstone.

As referred to herein, re-identification of a rough stone refers to the process of confirming that a stone is, in fact, the same physical stone as previously identified, and not a different stone.

As referred to herein, a rough gemstone refers to a stone that has not been cut to form facets.

What is claimed is:

1. A method of re-identifying a rough gemstone, the method comprising:
providing a three-dimensional (3D) model of a first rough gemstone;
generating a series of virtual two-dimensional (2D) silhouette images of the 3D model;
processing each 2D image of the series of virtual 2D silhouette images to obtain a dataset associated with the first rough gemstone;
comparing the dataset of the first rough gemstone with an existing dataset of a rough gemstone; and
where the dataset of the first rough gemstone and the existing dataset match each other, re-identifying the first rough gemstone as the same rough gemstone from which the existing dataset was obtained.

2. The method as claimed in claim 1, further comprising capturing a virtual 2D silhouette image of the 3D model from each of a plurality of virtual viewpoints in a geodesic arrangement around the 3D model.

3. The method as claimed in claim 1, wherein processing each 2D image of the series of virtual 2D silhouette images comprises converting each said 2D image into a set of geometric shapes that characterise a silhouette of the first rough gemstone present in said 2D image.

4. The method as claimed in claim 3, wherein the set of geometric shapes is based upon one or more of a longest chord of the silhouette, an orthospread, and a convex hull deviance.

5. The method as claimed in claim 1, wherein the dataset comprises a series of numerical features derived from each of the 2D images of the series of virtual 2D silhouette images.

6. The method as claimed in claim 5, wherein the numerical features derived from each of the 2D images comprise thirty-two features to which four statistical operations are applied.

7. The method as claimed in claim 5 or 6, wherein the numerical features include a measurement of one or more of blockiness, symmetry, normalised inverted longest chord, Hu's moments, orthonormal dispersion ratio, convex hull area ratio, standard convex hull deviance, normalised convex hull deviance, convex hull deviance ratio, normalised missing perimeter lengths, concave segment perimeter ratio, area and perimeter, longest chord, and orthospread.

8. The method as claimed in claim 7, wherein the measurement is obtained from one or more of the rough gemstone and a convex hull of the rough gemstone.

9. The method as claimed in claim 5, further comprising calculating one or more of the maximum, minimum, mean and coefficient of variance of each of the series of numerical features.

10. The method as claimed in claim 1, wherein one or more of: the dataset associated with the first rough gemstone; the existing dataset; and a result of the comparison between the datasets forms part of a distributed ledger, such as a blockchain.

11. The method as claimed in claim 1, wherein providing the 3D model of the first rough gemstone comprises:
    obtaining a series of 2D silhouette images of the rough gemstone using one or more physical image capture devices; and
    processing said series of 2D silhouette images to generate the 3D model of the rough gemstone.

12. The method as claimed in claim 11, wherein said one or more physical image capture devices are stationary while the series of 2D silhouette images are obtained.

13. The method as claimed in claim 11, further comprising illuminating the rough gemstone with collimated lighting while obtaining the series of 2D silhouette images.

14. The method as claimed in claim 1, wherein the 3D model is a surface model of the rough gemstone.

15. The method as claimed in claim 1, further comprising obtaining the existing dataset as part of a process of sorting the output of a mine, and wherein re-identifying the rough gemstone comprises confirming that the rough gemstone is originated from the mine.

16. The method as claimed in claim 1, wherein the rough gemstone is a rough diamond.

17. The method as claimed in claim 1, further comprising comparing the dataset of the first rough gemstone with a plurality of existing datasets of rough gemstones stored in a database.

* * * * *

UNITED STATES PATENT AND TRADEMARK OFFICE
CERTIFICATE OF CORRECTION

| | | |
|---|---|---|
| PATENT NO. | : 11,893,809 B2 | Page 1 of 1 |
| APPLICATION NO. | : 17/620477 | |
| DATED | : February 6, 2024 | |
| INVENTOR(S) | : Qi He Hong | |

It is certified that error appears in the above-identified patent and that said Letters Patent is hereby corrected as shown below:

In the Claims

In Column 14, Claim 7, Line 60, that reads "The method as claimed in claim 5 and 6," should read -- The method as claimed in claim 5, --

Signed and Sealed this
Thirty-first Day of December, 2024

Derrick Brent
*Acting Director of the United States Patent and Trademark Office*